United States Patent [19]

Osei-Gyimah et al.

[11] Patent Number: 5,288,693
[45] Date of Patent: Feb. 22, 1994

[54] 2-(3-OXOALK(EN)YL)-3-ISOTHIAZOLONES AND DERIVATIVES AS ANTIMICROBIAL AGENTS

[75] Inventors: Peter Osei-Gyimah, Horsham; Barry C. Lange, Lansdale, both of Pa.

[73] Assignee: Rohm and Haas Company, Philadelphia, Pa.

[21] Appl. No.: 83,958

[22] Filed: Jun. 25, 1993

[51] Int. Cl.$^5$ .................. A01N 43/80; C07D 275/03; C07D 275/04
[52] U.S. Cl. .................................... 504/156; 514/372; 514/373; 548/209; 548/213
[58] Field of Search ................ 548/209, 213; 514/372, 514/373; 504/156

[56] References Cited

U.S. PATENT DOCUMENTS

| | | | |
|---|---|---|---|
| 3,761,489 | 9/1973 | Grivas | 514/372 |
| 4,325,201 | 4/1982 | Lewis et al. | 514/372 |
| 4,654,354 | 3/1987 | Shroot et al. | 514/372 |

FOREIGN PATENT DOCUMENTS 443821 8/1991 European Pat. Off. .

Primary Examiner—Jospeh Paul Brust
Assistant Examiner—MarySusan H. Gabilan
Attorney, Agent, or Firm—Michael B. Fein

[57] ABSTRACT

Antimicrobial compounds of the formula

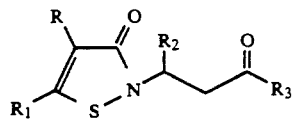

or

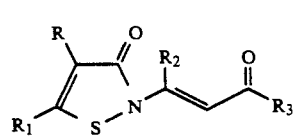

wherein
R is hydrogen, halogen or ($C_1$-$C_4$)alkyl group;
$R_1$ is hydrogen or halogen; alternatively, R and R1 may be taken together with the carbons to which they are attached to form a 5- to 7-membered carbocyclic ring, said ring optionally being aromatic;
$R_2$ is hydrogen or ($C_1$-$C_3$)alkyl group; and
R3 is hydrogen, substituted or unsubstituted ($C_1$-$C_{18}$)alkyl, substituted or unsubstituted ($C_2$-$C_{18}$)alkenyl, substituted or unsubstituted ($C_2$-$C_{18}$)alkynyl, substituted or unsubstituted ($C_4$-$C_8$)cycloalkyl or cycloalkenyl, substituted or unsubstituted ($C_6$-$C_{10}$)aryl or arylalkyl group are disclosed.

7 Claims, No Drawings

2-(3-OXOALK(EN)YL)-3-ISOTHIAZOLONES AND DERIVATIVES AS ANTIMICROBIAL AGENTS

BACKGROUND OF THE INVENTION

1. Field of the Invention

This invention relates to the field of new derivatives of 3-isothiazolones, their preparation, and their use in controlling living organisms.

2. Description of the Prior Art

3-Isothiazolones have generated high commerical interest as microbicides to prevent spoilage caused by microorganisms in a large number of aqueous and non-aqueous products subject to such spoilage. 3-Isothiazones are highly effective microbicides (as used herein, "microbicides" includes bactericides, fungicides, and algaecides and microbicidal activity is intended to include both the elmination of and inhibition or prevention of growth of microbial organisms such as bacteria, fungi, and algae) and are useful in a broad range of applications.

Lewis et al., U.S. Pat. Nos. 3,761,488; 3,544,580; 3,835,150; 3,706,757; 3,755,224; and 4,105,431, all assigned to Rohm and Haas Co., the same assignee as the present invention, disclose 3-isothiazolone compounds.

U.S. Pat. No. 3,835,150 to Lewis, also assigned to Rohm and Haas Co., disclosed certain acrylic iso-thiazolonyl derivatives. Lewis discloses the reaction of certain 3-hydroxyisothiazoles with acetylenic compounds, such as methyl propiolate, propiolnitrile, N,N-dimethylpropiolamide, and propiolic acid in the presence of a base catalyst such as triethyl amine or a quaternary ammonium hydroxide. While this patent discloses other potential reactions, only a few specific products are provided. Compound A below (compound 16 disclosed in Lewis '150 at Table I), as well as the other possible products listed in Example 22 of the '150 patent, result from the reaction occurring at the oxygen, not at the nitrogen of the 3-hydroxyisothiazoles.

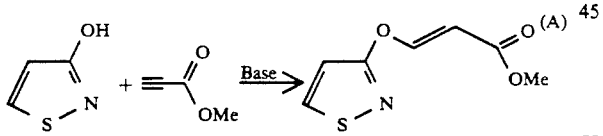

Lewis '150 further discloses the reactions of certain active halogen compounds with 3-hydroxyisothiazoles. Of particular note are the reactions of β-haloacrylats, β-haloacrylamides, and β-haloacrylonitrile with 3-hydroxyisothiazoles to yield compounds of structure B below, wherein X is halogen and Z is alkoxy, amino or nitrile. The compounds exemplified in this patent show reaction at the oxygen only; no compounds corresponding to reaction at the nitrogen of the 3-hydroxyisothiazoles are reported.

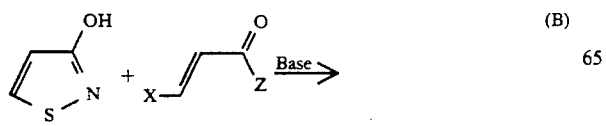

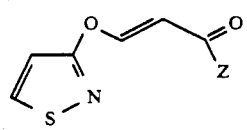

U.S. Pat. No. 4,105,431 to Lewis, also assigned to Rohm and Haas Co., discloses reacting vinyl acetate with a 3-hydroxyisothiazole to give a vinyl substituted isothiazolone, compound C below. The patent further discloses that mercuric salts can be advantageously used to catalyze the reaction.

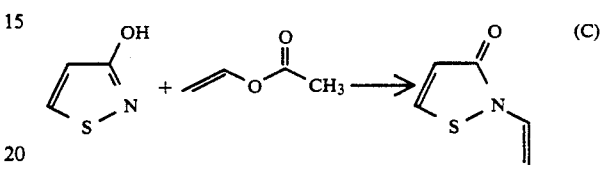

Also disclosed in this patent is the reaction of 3-hydroxyisothiazole with an appropriate haloalkene or haloalkyne to give the 2-alkenyl- or 2-alkynyl-3-isothiazolone, respectively. This reaction is that of a simple alkylation of the 3-hydroxyisothiazole nitrogen. An acid accepting base, such as a metal hydride or metal hydroxide, is normally used to catalyze this reaction.

SUMMARY OF THE INVENTION

Many of the antimicrobials of the prior art have toxicity and/or environmental problems. Prior reaction processes are incapable of preparing certain novel 3-isothiazolone compounds.

It is an object of the present invention to prepare novel 3-isothiazolone compounds which have efficacy against a broad spectrum of bacteria and fungi. It is a further object to provide a novel and versatile method of preparing certain 2-substituted-3-isothiazolones.

These objects, and others which will become apparent from the following disclosure, are achieved by the present invention which comprises in one aspect 3-isothiazolone compounds of the formula

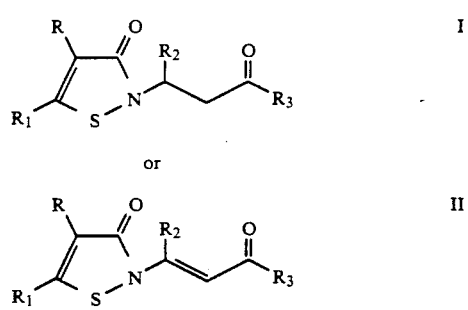

wherein

R is hydrogen, halogen or $(C_1-C_4)$alkyl group;

$R_1$ is hydrogen or halogen;

alternatively, R and R1 may be taken together with the carbons to which they are attached to form a 5- to 7-membered carbocyclic ring, said ring optionally being aromatic;

$R_2$ is hydrogen or $(C_1-C_3)$alkyl group;

and $R_3$ is hydrogen, substituted or unsubstituted $(C_1-C_{18})$alkyl, substituted or unsubstituted $(C_2-C_{18})$alkenyl, substituted or unsubstituted $(C_2-C_1$-

8)alkynyl, substituted or unsubstituted (C4–C8)cycloalkyl or cycloalkenyl, substituted or unsubstituted (C6–C10)aryl or arylalkyl group;

In another aspect, the invention comprises a method of preparing an isothiazolone of formula I or II above by reacting a 3-hydroxyisothiazole of the formula

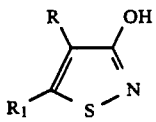

III wherein R and R1 are as defined above, with an α,β-unsaturated ketone or aldehyde of formula

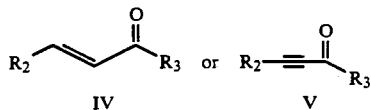

wherein R2 and R3 are as defined above.

A further aspect of the invention comprises using a composition comprising the compound(s), or the compound(s) itself to control the growth of microorganisms.

DETAILED DESCRIPTION AND THE PREFERRED EMBODIMENTS

The compounds of the invention are especially active and efficient antimicrobials.

The preferred substituents for R are hydrogen and halogen, with hydrogen being the most preferred. The preferred substituents for R1 are hydrogen and halogen. It is also preferred that R and R1 may be taken together along with the carbons to which they are attached to form a 5-membered carbocyclic ring.

The preferred substituents for R2 are hydrogen and $(C_1-C_3)$alkyl. The most preferred substituents for R2 are hydrogen and methyl.

R3 is preferably hydrogen, substituted or unsubstituted $(C_1-C_{18})$alkyl, $(C_2-C_{18})$alkenyl or $(C_2-C_{18})$alkynyl, $(C_3-C_7)$cycloalkyl, $(C_5-C_7)$cycloalkenyl, $(C_6-C_{10})$aryl or arylalkyl. More preferably, R3 is hydrogen, $(C_1-C_{18})$alkyl, $(C_4-C_8)$cycloalkenyl and substituted aryl. Most preferably, R3 is hydrogen, methyl, pentyl, benzoquinone and dimethoxyphenyl.

By a substituted alkyl, alkenyl or alkynyl group is meant an alkyl, alkenyl or alkynyl group having one or more of the hydrogen atoms replaced by another substituent group. Examples of such substituent groups include halogen, $(C_4-C_7)$cycloalkyl, $(C_5-C_7)$cycloalkenyl, $(C_1-C_6)$alkoxy, nitro, mercapto, acylamino and the like, or may be a ketone, ester or an aldehyde functional group.

By a substituted aryl group is meant a benzene, naphthalene, pyridine, furan, pyrrole, or a thiophene having one or more of the hydrogen atoms replaced by another substituent group. Examples of such substituent groups include halogen, methoxy, nitro, hydroxy, $(C_1-C_6)$alkoxycarbonyl and the like.

By a substituted arylakyl group is meant an arylalkyl group having one or more of the hydrogen atoms on either the aryl ring or alkyl chain replaced by another substituent group. Examples of such substituent groups include halogen, methoxy, hydroxy, nitro, alkoxycarbonyl, carbonyls, and the like.

Among the preferred compounds of formula I or II are the following:

1. 2-(3-Oxobutyl)-5-chloro-4-isothiazolin-3-one
2. 2-(3-Oxobutyl)-4-isothiazolin-3-one
3. 2-(3-Oxooctyl)-5-chloro-4-isothiazolin-3-one
4. 2-(3-Oxooctyl)-4-isothiazolin-3-one
5. 3-(5-Chloro-4-isothiazolin-3-one-2-yl)propionaldehyde
6. 3-(4-Isothiazolin-3-one-2-yl)propionaldehyde
7. 3-(4,5-Trimethylene-4-isothiazolin-3-one-2-yl)propionaldehyde
8. 2-(1-Methyl-3-oxobutyl)-5-chloro-4-isothiazolin-3-one
9. 2-[3-Oxo-3-(2,5-dimethoxyphenyl)propyl]-5-chloro-4isothiazolin-3-one
10. 2-[3-(5-Chloro-4-isothiazolin-3-one-2-yl)propionyl]-1,4-benzoquinone
11. 2-(3-Oxo-1-butene-4-yl)-5-chloro-4-isothiazolin-3-one.

The 2-(3-oxoalk(en)yl)-isothiazolones of the invention can be derivatized by known methods with alcohols and orthoformates to yield ketals and acetals and with alkoxylamine hydrochlorides to form oximes. For example, derivatization of compounds of formula 1 yield compounds:

12. 3-(5-Chloro-4-isothiazolon-3-one-2-yl)propionaldehyde diethyl acetal
13. 2-[(3-Methoxyimino)octyl]-5-chloro-4-isothiazolon-3-one.

Tables 1 and 2 show the structures and then physical data of the representative compounds of formulae I and II, respectively. Table 3 shows the structures and physical data for the derivatives of compounds of formula I.

TABLE 1

Structures and Physical Data of Representative Compounds of Formula I

| Comp. No. | R | R1 | R2 | R | Melting Point |
|---|---|---|---|---|---|
| 1 | H | Cl | H | CH3 | Oil |
| 2 | H | H | H | CH3 | Oil |
| 3 | H | Cl | H | (CH2)4CH3 | 57–58° C. |
| 4 | H | H | H | (CH2)4CH3 | Oil |
| 5 | H | Cl | H | H | Oil |
| 6 | H | H | H | H | Oil |
| 7 | —CH2CH2CH2— | | H | H | 66–68° C. |
| 8 | H | Cl | CH3 | CH3 | Oil |
| 9 | H | Cl | H | Ph(2,5-di-OCH3) | 75–77° C. |
| 10 | H | Cl | H | 1,4-Benzoquinone | 181–183° C. |

TABLE 2

Structures and Physical Data of Representative Compounds of Formula II

| Comp. No. | R | R1 | R2 | R3 | Melting Point |
|---|---|---|---|---|---|
| 11 | H | Cl | H | CH3 | Oil |

TABLE 3

Structures and Physical Data of Derivatives of Compounds of Formula I

| Comp. No. | | Melting Point |
|---|---|---|
| 12 | (structure) | Oil |

TABLE 3-continued

Structures and Physical Data of Derivatives of
Compounds of Formula I

| Comp. No. | | Melting Point |
|---|---|---|
| 13 | 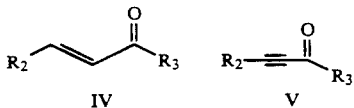 | Oil |

It has been surprisingly found that 3-hydroxyisothiazole and its derivatives, formula III, react with $\alpha,\beta$-unsaturated carbonyl compounds to give novel, keto-functionalized, 2-(3-oxoalk(en)yl)-isothiazolones in high yields.

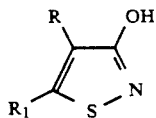
III

This reaction has been found to be general for a variety of 3-hydroxyisothiazoles and for a variety of $\alpha,\beta$-unsaturated carbonyl compounds. The $\alpha,\beta$-unsaturated carbonyl compounds useful in this invention are vinyl ketones and aldehydes and acetylenic ketones and aldehydes of formula IV and V respectively.

IV     V

The 3-hydroxyisothiazole wherein R and $R_1$ are hydrogen can be prepared by the method of Crow et al., *J. Org. Chem.*, 30, 2660 (1965). Substituted 3-hydroxyisothiazoles can be prepared according to the method of Miller et al., *J. Heterocyclic Chem.*, 8, 581 (1971). 4,5-Trimethylene-3-hydroxyisothiazole can be prepared according to the method of Maignon et al., U.S. Pat. No. 4,851,451.

The $\alpha,\beta$-unsaturated carbonyl compounds useful in this invention are commercially available or may be prepared by a variety of known methods. Several of these known methods may be found in Milstein et al., *J. Amer. Chem. Soc.*, 100, 3636 (1978); Ponticello et al., *J. Polymer Sci.*, 12, 985 (1974); Stork et al., *Tetrahedron Lett.*, 27, 2755 (1972); d'Angelo et al., *Tetrahedron Lett.*, 32, 3063 (1991); Kobayashi et al., *Tetrahedron Lett.*, 35, 7245 (1991); Janowitz et al., *Helv Chim. Acta*, 74, 1352 (1991); Bhamare et al., *Tetrahedron Lett.*, 33, 4439 (1991); and Girotra et al., *J. Med. Chem.*, 35, 3474, (1992). Also, $\alpha,\beta$-unsaturated carbonyl equivalents, such as enol ethers, may be employed. An example of such an $\alpha,\beta$-unsaturated carbonyl equivalent is 2-methoxy-1,3-butadiene. 2-Methoxy-1,3-butadiene can be prepared according to the method of Dolby et al., *Org. Prep. and Proc.*, 1 (4), 229 (1969). Also useful are trialkylsilylenol ethers, such as 2-trimethylsiloxy-1,3-butadiene, prepared according to the method of Jung et al., *Tetrahedron L ett.*, 2935 (1976).

The following scheme shows the reaction of a hydroxyisothiazole with either a vinyl ketone or an acetylenic ketone to yield the compounds of the invention of formula I or II (wherein X and Y have been taken together to form a carbonyl)

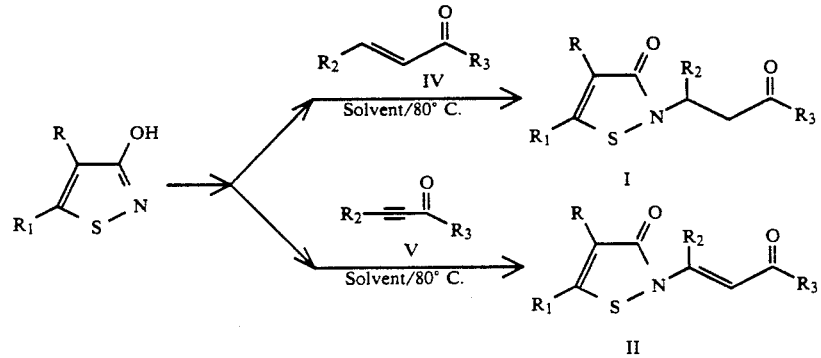

wherein R, $R_1$, $R_2$, and $R_3$ are as described above. Equimolar quantities of the hydroxyisothiazole and the $\alpha,\beta$-unsaturated carbonyl compound are normally used in this reaction. However, an excess of the vinyl or the acetylenic ketone or aldehyde may be employed. The addition of an acid such as p-toluenesulfonic acid or propionic acid in catalytic amounts does not inhibit the reaction.

The reaction of the hydroxyisothiazole with the $\alpha,\beta$-unsaturated carbonyl compound proceeds within 1 to 72 hours at a temperature within the range of 25°-100° C. When an $\alpha,\beta$-unsaturated carbonyl equivalent is used, the addition of small amounts of hydroquinone may be required. Organic solvents are employed in this reaction. These solvents may be a single solvent or mixtures of suitable solvents. Examples of suitable solvents include alkyl esters, hydrocarbons and aromatic hydrocarbons. Preferred solvents include ethyl acetate, toluene, benzene, and xylene. The most preferred solvent is toluene.

Suitable vinyl and acetylenic ketones and aldehydes which may be used in preparing the compounds of the invention include, but are not limited to: acrolein, methyl vinyl ketopne, 1-octen-3-one, 3-butyn-2-one, 1-octyn-3-one, 3-penten-2-one, benzoylacetylene, 1-hexen-3,5-dione, 1-hepten-3,6-dione, 2-acryloylthiophene, 2-acryloylpyrrole, 5-(2-hydroxyphenyl)-1-penten-3-one, phenyl vinyl ketone, cyclohexyl vinyl ketone, methyl 3-oxo-4-pentenoate, 2-(6-heptenyl-2-one)furan, 4-methylphenyl vinyl ketone, 3-acryloyl-cyclopentanone, 2,5-dimethoxyphenyl vinyl ketone, 2-acryloyl-1,4-benzoquinone, 3,4,5-trimethoxyphenyl vinyl ketone, and ethyl 4-oxo-5-hexenoate.

The carbonyl functionality on the side chain of the compounds of the invention undegoes the usual carbonyl transformations. For example, acetals of the invention compounds can be prepared by reacting compounds of formulae I or II (where X and Y are taken together to form a carbonyl) with a trialkyl orthoformate in the presence of an acid catalyst, such as p-toluenesulfonic acid, in a suitable solvent, such as ethanol. Oximes of the compounds of the invention can be prepared by reacting the 2-oxoalk(en)ylisothiazolones with methoxylamine hydrochloride in a suitable solvent, such as ethanol, in the presence of a base, such as triethylamine. This reaction occurs at room temperature and is complete in 1 to 24 hours. The carbonyl can also undergo reaction with alkylating agents such as Grignard reagents. Compound 1 reacts with methyl Grignard in tetrahydrofuran at 25°-80° C. over 1-6 hours.

When used as microbicides, the compounds according to formula I or II are surprisingly effective bactericides, algicides and fungicides and are especially useful to protect cosmetic agents, cutting oils, soap or synthetic detergent, stabilizers, film forming materials, and other applications where microbicides have been used in the past. The preferred microbicidal utilities of the compositions are to protect wood, paint, adhesive, glue, paper, textile, leather, plastics, cardboard, lubricants, cosmetics, food, caulking, feed and industrial cooling water from microbial attack.

The compounds of the invention may be used in admixture with other microbicides.

The compounds of the invention are introduced onto, into, or at a locus subject to microbial attack to control microbicidal growth. Suitable methods of application of the compounds of the invention to control bacteria, algae, fungi and the like are well known in the art.

The amount of the compound to be used in microbicidal applications depends upon the application. The useful amounts for a particular application are similar to amounts used for other microbicidal compounds.

The following specific examples are presented to illustrate various aspects of the present invention but are not to be construed as limitations thereof.

EXAMPLES

Example 1: Preparation of 2-(3-Oxobutyl)-5-chloro-4-isothiazolin-3-one (Compound 1)

A solution of 5-chloro-3-hydroxyisothiazole (1.5 g, 0.011 mole), 2-trimethylsiloxy-1,3-butadiene (5.6 g, 0.04 mole) and 0.5 g of hydroquinone in 20 ml of toluene was heated at 80° C. for 96 hours. After cooling, the mixture was concentrated in vacuo. The residual oil was dissolved in diethyl ether and washed with saturated NaHCO$_3$ solution and then with water. After drying (MgSO$_4$) and concentrating the solution, the residual oil was purified by column chromatography on silica gel, using diethyl ether/methanol (9/1) as eluant. Compound 1 was obtained as an oil, 0.3 g; IR (neat) 1625,1650 cm$^{-1}$; NMR (CDCl$_3$) δ6.25 (s,1H); 4.0 (t, 2H); 2.9 (t,2H); 2.2 (s, 3H).

Example 2: Preparation of 2-(3-Oxobutyl)-5-chloro-4-isothiazolin-3-one) (Compound 1)

A solution of 0.5 g (0.0037 mole) of 5-chloro-3-hydroxyisothiazole and methyl vinyl ketone (1.0 g, 0.014 mole) in 15 ml of toluene was heated at 80° C. for 24 hours. After cooling and removal of toluene and excess reagent by rotary evaporation, the residual oil was purified by column chromatography on silica gel, using diethyl ether/methanol (9/1) as eluant. Compound 1 was obtained as an oil; 0.65 g (85%); IR (neat) 1725,1650 cm$^{-1}$; NMR (CDCl$_3$) δ6.25 (s,1H); 4.0 (t,2H); 2.9 (t,2H); 2.2 (s,3H).

Example 3: Preparation of 2-(3-Oxooctyl)-4-isothiazolin-3-one (Compound 4)

A solution of 3-hydroxyisothiazole (2.0 g, 0.02 mole) and n-amyl vinyl ketone (3.7 g, 0.03 mole) in 20 ml of toluene was heated at 80° C. for 6 hours. Upon cooling, the reaction mixture was concentrated by rotary evaporation. The residual oil was purified by column chromatography on silica gel, using diethyl ether/methanol (4/1) as eluant. Compound 4 was obtained as an oil; 4.2 g (93%)IR (neat) 1650, 1710 cm$^{-1}$; NMR (CDCl$_3$) δ8.15 (d,1H); 6.25 (d,1H); 4.05(t,2H); 2.90 (t,2H); 2.4(t,2H); 1.6 (m,2H); 1.3 (m,4H); 0.9 (t,3H).

Example 4: Preparation of 3-(4,5-Trimethylene-4-isothiazolin-3-one-2-yl)propionaladehyde (Compound 7)

A stirred suspension of 4,5-trimethylene-3-hydroxyisothiazole (1.0 g, 0.007 mole) and acrolein (4.8 g, 0.086 mole) in 20 ml of toluene was heated to 70° C. The resulting solution was held at 70° C. for 2.5 hours and then cooled and concentrated. The residual brown oil was purified by column chromatography on silica gel, using ethyl acetate as eluant. The desired compound was obtained as a white solid; 0.98 g; mp 66°-68° C.; IR (KBr) 1710,1625 cm$^{-1}$; NMR (CDCl$_3$) δ9.9 (s,1H); 4.05 (t,2H); 2.95 (m, 4H); 2.65 (t,2H); 2.45 (m 2H).

Example 5: Preparation of 2,5-Dimethoxyphenyl vinyl carbinol

A solution of 2,5-dimethoxybenzaldehye (12.0 g, 0.072 mole) in 50 ml of dry THF was added dropwise to 100 ml of 1M solution of vinyl magnesium bromide in THF while keeping the reaction mixture at room temperature with cooling. The mixture was stirred for 4 hours at room temperature and then quenched with saturated NH$_4$Cl solution. The layers were separated and the aqueous portion was extracted with diethyl ether. The combined organic portion was washed with water, dried (MgSO$_4$), and concentrated. The resulting oil, 13.4 g, was sufficiently pure for the next reaction; IR (neat) 3500 cm$^{-1}$); NMR (CDCl$_3$) δ6.7-7.0 (m,3H); 6.0-6.2 (m, 1H); 5.1-5.3 (m,3H); 3.75 (two singlets, 6H); 3.16 (br,1H).

Example 6: Preparation of 2,5-Dimethoxyphenyl vinyl ketone

Activated MnO$_2$ (100 g) was added in portions to a mechanically stirred solution of 2,5-dimethoxyphenyl vinyl carbinol (12.5 g, 0.064 mole) in 250 ml of methylene chloride. The mixture was stirred at room temperature for 24 hours and then filtered through a patch of Celite. The filtrate was concentrated to give a brown oil which was purified by column chromatography on silica gel, using diethyl ether/hexane (1/1) as eluant. The compound was obtained as a light brown oil; 7.2 g; IR (neat) 1680 cm$^{-1}$; NMR (CDCl$_3$) δ6.85-7.1 (m,4H); 6.3 (d,1H); 5.8 (d,1H); 3.8 and 3.85 (two singlets,6H).

Example 7: Preparation of 2-Acryloyl-1,4-benzoquinone

To a stirred solution of 2,5-dimethoxyphenyl vinyl ketone (2.5 g, 0.013 mole) in 25 ml of acetonitrile at 0°

C. was added dropwise over 3 minutes an aqueous solution of $(NH_4)_2Ce(NO_2)_6$ (17.9 g, 0.033 mole) in 30 ml of water. After the addition, the dark brown mixture turned to yellowish-brown within 5 minutes. At that point, the mixture was poured into water and extracted with methylene chloride. The methylene chloride portion was washed twice with water and then with brine. After drying ($MgSO_4$), the solvent was removed to give a brown oil, which was purified by column chromatography on silica gel, using diethyl ether/hexane (1/1) as eluant. The product was obtained as a reddish/orange, semi-solid residue; 0.8 g; IR (neat) 1670 cm$^{-1}$; NMR ($CDCl_3$) $\delta$5.95 (d,1H); 6.5-7.2 (m5H).

Example 8: Preparation of 2-[3-(5-Chloro-4-isothiazolin-3-one-2-yl)propionyl]-1,4-benzoquinone (Compound 10)

A stirred solution of 2-acryloyl-1,4-benzoquinone (1.0 g, 0.007 mole) and 5-chloro-3-hydroxyisothiazole (0.81 g, 0.006 mole) in 20 ml of toluene was heated at 80° C. for 4 hours. Upon cooling, the precipitate which formed during the reaction period was removed by filtration and recrystallized from ethyl acetate/acetone mixture. A gray/tan solid was obtained; 0.85 g; mp 181°-183° C.; IR (KBR) 1635 cm$^{-1}$ (broad);NMR (acetone-d$_6$) $\delta$7.35 (s,1H); 7.15 (d 1H); 6.85 (d 1H); 6.35 (s,1H); 4.2 (t,2H); 3.52 (t,2H).

Example 9: Preparation of 2-(2-Oxo-3-buten-4-yl)-5-chloro-4-isothiazolin-3-one (Compound 11)

A stirred solution of 5-chloro-3-hydroxyisothiazole (1.5 g, 0.011 mole), 1-butyn-3-one (3.5 g, 0.05 mole) and p-toluenesulfonic acid (0.02 g) in 25 ml of toluene was heated at 80° C. for 24 hours. Upon cooling, the dark brown reaction mixture was concentrated and the residual oil was column chromatographed on silica gel, using diethyl ether/hexane as eluant. Compound 11 was obtained as a yellowish solid; 1.8 g; mp 137°-139° C.; IR (KBr) 1675, 1620 cm$^{-1}$; NMR ($CDCl_3$) $\delta$8.2 (d,1H,J=13.9 Hz); 6.35 (s,1H); 5.85 (d,1H,J=13.9 Hz); 2.35 (s,3H).

Example 10: Preparation of 3-(5-Chloro-4-isothiazolin-3-one-2-yl)propionaldehyde diethyl acetal (Compound 12)

A solution of compound 5 (2.5 g, 0.013 mole), triethyl orthoformate (3.87 g, 0.026 mole) in 20 ml ethanol and p-toluenesulfonic acid (35 mg) was refluxed for 18 hours. Upon cooling, the mixture was treated with 0.2 ml of triethylamine and extracted with diethyl ether. The extract was then washed successively with $NaHCO_3$ solution, water and brine. After drying ($MgSO_4$), the solvent was removed in vacuo. The residual brown oil was purified by column chromatography on silica gel, using diethyl ether/hexane (4/1) as eluant. The product was obtained as a light brown oil; 2.2 g; IR (neat) 1625 cm$^{-1}$; NMR ($CDCl_3$) $\delta$6.3 (s,1H); 4.6 (t,1H); 3.85 (t, 2H); 3.4-3.8 (m,4H); 2.0 (q,2H); 1.2 (t,6H).

Example 11: Preparation of 2-[(3-Methoxyimino)octyl]-5-chloro-4-isothiazolin-3-one (Compound 13)

A solution of methoxyamine hydrochloride (0.22 g, 0.0026 mole) and triethylamine (0.304 g, 0.003 mole) in 15 ml of ethanol was stirred for 30 minutes at room temperature. This solution was added dropwise over a 30 minute period to a stirred solution of compound 3 (0.66 g, 0.0025 mole) in 10 ml of ethanol. The mixture was stirred under nitrogen at room temperature for 24 hours and then poured into water and extracted with methylene chloride. The organic extract was washed with dilute aqueous HCl and then with water. After drying ($MgSO_4$) and concentrating the solution, the residual oil was purified by column chromatography on silica gel, using hexane/diethyl ether (1/1) as eluant. Compound 13 was obtained as an oilly mixture of isomers; 0.27 g; IR (neat) 1650 cm$^{-1}$; NMR ($CDCl_3$) $\delta$6.25 (s, 1H); 3.8-4.1 (m5H); 2.5-2.7 (m2H); 2.1-2.3 (m2H); 1.2-1.5 (m,6H); 1.8-1.95 (m,3H).

Example 12: Biological Activity

The isothiazolone compounds of this invention demonstrated anti-microbial activity against bacteria and fungi. A stock solution of the test compound was made in dimethyl sulfoxide at 13,000 ppm and then diluted 26-fold to give a starting concentration of 500 ppm. The antimicrobial activity was evaluated by a two-fold serial dilution of the statring concentration of 500 ppm, using Trypticase Soy Broth medium at pH 7.0. The test organisms used to demonstrate antimicrobial activity are listed in Table 4. The minimum inhibitory concentration (MIC) of compounds 1-13 against the test organisms are shown in Table 5.

TABLE 4

| Microorganisms used in the Antimicrobial Test | |
| --- | --- |
| Name | Abbreviations Used |
| Bacteria | |
| Pseudomonas aeruginosa | Psae |
| Escherichia coli | Ecol |
| Staphlococcus aureus | Saur |
| Fungus | |
| Aspergillus niger | Anig |

TABLE 5

| Antimicrobial Activity (MIC, ppm) of Compounds 1-13 | | | | |
| --- | --- | --- | --- | --- |
| Comp No. | Psae | Ecol | Saur | Anig |
| 1 | 8 | 0.5 | 0.5 | 4 |
| 2 | 125 | 16 | 32 | 500 |
| 3 | 32 | 1 | 2 | 1 |
| 4 | >500 | 64 | 32 | 4 |
| 5 | 8 | 1 | 8 | 2 |
| 6 | 64 | 125 | 64 | 16 |
| 7 | 250 | 32 | 64 | 500 |
| 8 | 32 | 8 | 8 | 16 |
| 9 | 64 | 16 | 1 | 2 |
| 10 | 64 | 8 | 4 | 125 |
| 11 | 32 | 8 | 16 | 16 |
| 12 | 500 | 125 | 32 | 32 |
| 13 | 125 | 16 | 1.0 | 64 |

While this invention has beed described in sufficient detail for those skilled in the art to be able to make and use it, various modifications, and improvements should become apparent from the foregoing disclosure without departing from the spirit and scope of the invention.

What is claimed is:

1. Antimicrobial compounds of the formula

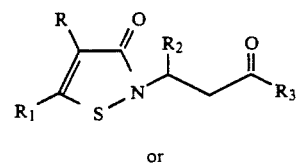

I or

-continued

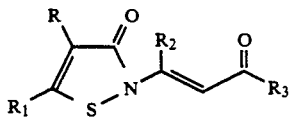

II wherein

R is hydrogen, halogen, or $(C_1-C_4)$alkyl group;

$R_1$ is hydrogen or halogen; alternatively, R and R1 may be taken together with the carbons to which they are attached to form a 5- to 7-membered carbocyclic ring, said ring optionally being aromatic;

$R_2$ is hydrogen or $(C_1-C_3)$alkyl group; and

R3 is hydrogen, substituted or unsubstituted $(C_1-C_{18})$, substituted or unsubstituted $(C_2-C_{18})$alkenyl, substituted or unsubstituted $(C_2-C_{18})$alkynyl, substituted or unsubstituted $(C_4-C_8)$cycloalkyl or cycloalkenyl, or a substituted or unsubstituted arylalkyl group.

2. Compound according to claim 1 wherein R is hydrogen and $R_1$ is hydrogen or chlorine.

3. Compound according to claim 1 wherein $R_2$ is methyl.

4. Compound according to claim 1 wherein $R_3$ is selected from the group consisting of hydrogen, methyl, pentyl, and 1,4-benzoquinone.

5. Compound according to claim 1 wherein said compounds are selected from the group consisting of
2-(3-Oxobutyl)-5-chloro-4-isothiazolin-3-one;
2-(3-Oxobutyl)-4-isothiazolin-3-one;
2-(3-Oxooctyl)-5-chloro-4-isothiazolin-3-one;
2-(3-Oxooctyl)-4-isothiazolin-3-one;
3-(5-Chloro-4-isothiazolin-3-one-2-yl)propionaldehyde;
3-(4-Isothiazolin-3-one-2-yl)propionaldehyde;
3-(4,5-Trimethylene-4-isothiazolin-3-one-2-yl)propionaldehyde;
2-(1-Methyl-3-oxobutyl)-5-chloro-4-isothiazolin-3-one;
2-[3-(5-Chloro-4-isothiazolin-3-one-2-yl)propionyl]-1,4-benzoquinone; and
2-(3-Oxo-1-buten-4-yl)-5-chloro-4-isothiazolin-3-one.

6. Process of inhibiting the growth of microorganisms comprising introducing a microbicidally effective amount of one or more compounds according to claim 1 onto, into, or at a locus subject to microbial attack to control microbial growth.

7. Process according to claim 6 wherein said locus is selected from the group consisting of wood, paint, adhesive, glue, paper, textile, leather, plastics, cardboard, lubricants, cosmetics, food, caulking, feed and industrial cooling water.

* * * * *